United States Patent
Lin et al.

(10) Patent No.: US 9,164,077 B2
(45) Date of Patent: Oct. 20, 2015

(54) BIOLOGICAL DETECTION DEVICE AND METHOD UTILIZING LCPCF FILM FOR TESTING LIQUID FORM SAMPLES CONTAINING TRIGLYCERIDE/HDL DISPOSED THEREON

(75) Inventors: Yi-Hsin Lin, Hsinchu County (TW); Wei-Lin Chu, Kaohsiung (TW); Li-Ching Wu, Tainan (TW)

(73) Assignees: NATIONAL CHIAO TUNG UNIVERSITY, Hsinchu (TW); CHI MEI MEDICAL CENTER, Tainan (TW)

( * ) Notice: Subject to any disclaimer, the term of this patent is extended or adjusted under 35 U.S.C. 154(b) by 436 days.

(21) Appl. No.: 13/595,648

(22) Filed: Aug. 27, 2012

(65) Prior Publication Data

US 2013/0167621 A1 Jul. 4, 2013

(30) Foreign Application Priority Data

Dec. 29, 2011 (TW) .............................. 100149671 A

(51) Int. Cl.
*G01N 33/00* (2006.01)
*G01N 33/49* (2006.01)
*B01L 3/00* (2006.01)

(52) U.S. Cl.
CPC .......... *G01N 33/49* (2013.01); *B01L 3/502792* (2013.01); *B01L 2400/0427* (2013.01)

(58) Field of Classification Search
CPC ................... B01L 3/502792; B01L 2400/0427
See application file for complete search history.

(56) References Cited

U.S. PATENT DOCUMENTS

| 6,478,912 | B2 | 11/2002 | Gaub et al. |
| 7,795,038 | B2 | 9/2010 | Jones et al. |
| 7,811,780 | B2 | 10/2010 | Katayama et al. |
| 7,838,631 | B2 | 11/2010 | Yamashita et al. |

(Continued)

FOREIGN PATENT DOCUMENTS

WO    WO 03/058239    7/2003

OTHER PUBLICATIONS

Lin et al., Droplet manipulation on a liquid crystal and polymer composite film, Aug. 17, 2010, Proc. SPIE 7775, Liquid Crystals XIV, 77750M, p. 1-6.*

(Continued)

*Primary Examiner* — Hezron E Williams
*Assistant Examiner* — Truong Phan
(74) *Attorney, Agent, or Firm* — Muncy, Geissler, Olds & Lowe, P.C.

(57) ABSTRACT

The present invention discloses a biological detection device and a detecting method. The biological detection device comprises a substrate, an electric field unit, a liquid crystal/polymer composite film (LCPCF), a power supply, a processing unit, and an image sensor. Because of the electrically tunable orientations of the liquid crystal (LC) director anchored among the polymer grains, the wettability of the LCPCF changes with an applied electric field. As a result, we can manipulate a blood droplet on the LCPCF by a wettability gradient owing to the distribution of LC directors on the LCPCF. The motion states of the blood droplet can be related to the various qualities of the blood, and finally determines the health of the test sample. The change of contact angle of blood on LCPCF and the blood droplet motion on LCPCF indicate the concentration of TG and the concentration of HDL.

14 Claims, 15 Drawing Sheets

(56) References Cited

U.S. PATENT DOCUMENTS

2005/0048599 A1* 3/2005 Goldberg et al. ............... 435/34
2006/0263033 A1* 11/2006 Lahann et al. ................ 385/147

OTHER PUBLICATIONS

Chiu, Ya-Ping; Shen, Cheng-Yu; Wang, Wen-Ching; Ting-Yu Chu; Lin, Yi-Hsin, "Electrically surface-driven switchable wettability of liquid crystal/polymer composite film,", Mar. 2010, Applied Physics Letters, vol. 96, No. 13, pp. 131902,131902-3, p. 1-4.*

Lin et al., Droplet manipulation on a liquid crystal and polymer composite film, Aug. 18, 2010, SPIE 7775, Liquid Crystals XIV, p. 1-6.*

Chiu et al., Electrically surface-driven switchable wettability of liquid crystal/polymer composite film, Mar. 31, 2010, Applied Physics Letters 96, pp. 1-4.*

* cited by examiner

BIOLOGICAL DETECTION DEVICE AND METHOD UTILIZING LCPCF FILM FOR TESTING LIQUID FORM SAMPLES CONTAINING TRIGLYCERIDE/HDL DISPOSED THEREON

CROSS-REFERENCE TO RELATED APPLICATION

This application claims the benefit of Taiwan Patent Application No. 100149671, filed on Dec. 29, 2011, in the Taiwan Intellectual Property Office, the disclosure of which is incorporated herein in its entirety by reference.

BACKGROUND OF THE INVENTION

1. Field of the Invention

The present invention relates to a detection device and a detecting method, and more particularly to a biological detection device that changes the hydrophilic property of a liquid crystal/polymer composite film to produce a serum droplet motion, and combines with an image sensor to detect biological information of the blood droplet to determine the health condition of the blood.

2. Description of Related Art

Conventional methods of testing triglyceride in blood is to take out serum composition from the blood by cell separation and add a specific testing agent after purification and a series of chemical conversions, and the extent of a color change of the testing agent is observed to measure the concentration of triglyceride. Medically, many factors must be taken into consideration for determining hyperlipidemia, and these factors include a comprehensive comparison of concentrations of triglyceride (TG), high density lipoprotein cholesterol (HDL), and low density lipoprotein cholesterol (LDL), and different chemical methods are used for testing each item, and thus the detection device and detecting method adopted require complicated and time-consuming processes.

In addition, the present hyperlipidemia testing technologies are still being developed with the targets of miniaturization, low cost and easy portability. At present, there is still a long waiting time in hospitals for patients requiring to have a physical examination to check whether or not they are a risk group of hyperlipidemia.

As disclosed in U.S. Pat. No. 6,478,912B2, a primer is coated on a metal surface, and a voltage is applied to switch the hydrophilic and hydrophobic properties. Although the primer can be used for protecting the metal surface, problems of a higher voltage (~1000V) and absolute temperature and unstable acid-alkali sensitivity still exist. As disclosed in PCT Pat. No. WO 03/058239A2, a dry-phase test is used for testing the concentration of triglyceride. Although this method can extend the retention period of triglyceride and can store triglyceride at room temperature, yet chemical analyses are required to test the concentration of triglyceride. During the chemical analysis process, the nature of the triglyceride may be damaged. As disclosed in U.S. Pat. No. 7,795,038B2, a testing board combined with a micro-channel and is used with molecules of a polysaccharide and poly-anions, and the testing board can be combined with HDL to induce an electrochemical reaction. An optical detection method is used to determine the concentration of HDL, but it is necessary to sieve extra molecules of LDL and VLDL fatty acids before the testing precision can be improved. This process is also complicated and time-consuming. As disclosed in U.S. Pat. No. 7,811,780B2, HDL test sample solution and testing solution are used to observe the concentration of the resultants or the residual of reactants to determine the concentration of HDL, but this method requires special solutions and complicated testing procedures, and the test can be used for the testing of HDL concentrations only. As disclosed in U.S. Pat. No. 7,838,631B2, HDL, VLDL, LDL and chylomicron with different physical properties can be used for manufacturing a simple filter device to separate HDL and other molecules, but this method cannot give the concentration levels of the HDL.

Although the aforementioned PCT and U.S. patents have provided various different detection devices and detecting methods to determine hyperlipidemia, these devices and methods still have many problems.

The prior art still lacks of a hypelipidemia detection device capable of detecting the concentration of triglyceride and high density liposome by a simple, easy and quick detecting method.

SUMMARY OF THE INVENTION

In view of the aforementioned problems of the prior art, it is a primary objective of the invention to provide a biological detection device and a detecting method that meet the user's self-using requirement and detect the concentration of triglyceride and high density liposome with a simple, easy and quick detecting method to obtain the health information of the user and the user's family.

To achieve the foregoing objective, the present invention provides a biological detection device for detecting a test sample in a liquid form, and the detection device comprises a substrate, a liquid crystal/polymer composite film, an electric field unit, a power supply, a processing unit and an image sensor. The liquid crystal/polymer composite film includes a liquid crystal director and a macromolecular polymer, and the test sample is placed on the liquid crystal/polymer composite film. The electric field unit is installed between the substrate and the liquid crystal/polymer composite film. The power supply is coupled to the electric field unit to supply a voltage to form an electric field, and the electric field is used to change the orientation of the liquid crystal director, so as to change the hydrophilic and hydrophobic properties of the liquid crystal/polymer composite film and drive the test sample to move. The processing unit is coupled to the power supply to control the power supply to supply a voltage to the electric field unit. The image sensor is coupled to the processing unit, and a test sample on a surface of the liquid crystal/polymer composite film is captured, and image data of the hydrophilic/hydrophobic motions are generated by the change of the electric field and provided for the processing unit. Wherein, the processing unit receives the image data and analyzes the biological property of the test sample according to the image data.

To achieve the aforementioned objective, the present invention provides a biological detecting method used for testing a test sample in a liquid form, and the biological detecting method comprises the following steps: A liquid crystal/polymer composite film is set on a substrate first, and then the test sample is placed on the liquid crystal/polymer composite film. An electric field unit is installed between the substrate and the liquid crystal/polymer composite film. A power supply is provided and coupled to the electric field unit to provide an electric field, and the electric field is used to change an orientation of the liquid crystal director to change hydrophilic and hydrophobic properties of the liquid crystal/polymer composite film to drive the test sample to move. A processing unit is connected to the power supply to control the power supply to supply the voltage of the electric field unit. An image sensor is installed to the processing unit to capture the test sample on a surface of the liquid crystal/ polymer composite film. Image data of a hydrophilic/hydrophobic motions generated are caused by a change of the electric field, and the image data are provided to the processing unit. Finally, the processing unit is used to receive the image data, and analyze a biological property of the test sample according to the image data.

To achieve the aforementioned objective, the present invention further provides a biological detecting method, used for testing a droplet in a liquid form and a predetermined concentration, and the biological detecting method comprises the following steps: The droplet is set on a macromolecular thin film, when a voltage is not applied, and then an image sensor is used to detect and capture contact angle image data of the droplet on a surface of the macromolecular thin film. Finally, the contact angle image data are collected, and a biological property of the droplet is analyzed according to the contact angle image data.

In summation, the biological detection device and the detecting method of the present invention have the following advantages:

(1) The present invention provides a simple and quick biological detecting method to detect the concentration of triglyceride and high density liposome, and use an electrically controlled surface polarity of a polymer thin film to make contact with a serum, and the serum concurrently has triglyceride and high density liposome. From the observation of the contact angle and the applied voltage, the concentration of triglyceride and high density liposome in the serum can be detected.

(2) The present invention can be applied to the biomedical field such as biosensors and micro-fluidic channel and provides new applications in the well-developed LCD industry.

(3) The present invention uses an electrically controlled method to change the distribution of surface polarity of the liquid crystal/polymer composite film, and applies the method for human blood detection. The biological detection device of present invention connects the processing unit to the power supply and the image sensor to capture the test sample on a surface of the liquid crystal/polymer composite film, generate image data of hydrophilic/hydrophobic motion caused by the change of electric field, and analyze a biological property of the test sample according to the image data.

(4) The present invention improves the long process of analyzing blood quality and allows users to know about the preliminary information of their blood in a timely manner and obtain physiological information easily without going through a complicated chemical analysis.

(5) At present, the LCD industry is well established, and the present invention provides an easy testing apparatus for LCD manufacturers, and allows designers to design the testing apparatus of different sizes for different quantity of test samples to achieve the effect of testing a large quantity of test samples quickly.

DETAILED DESCRIPTION OF THE PREFERRED EMBODIMENTS

The technical contents and characteristics of the present invention will be apparent with the detailed description of a preferred embodiment accompanied with related drawings as follows.

First Preferred Embodiment

Figure 1:
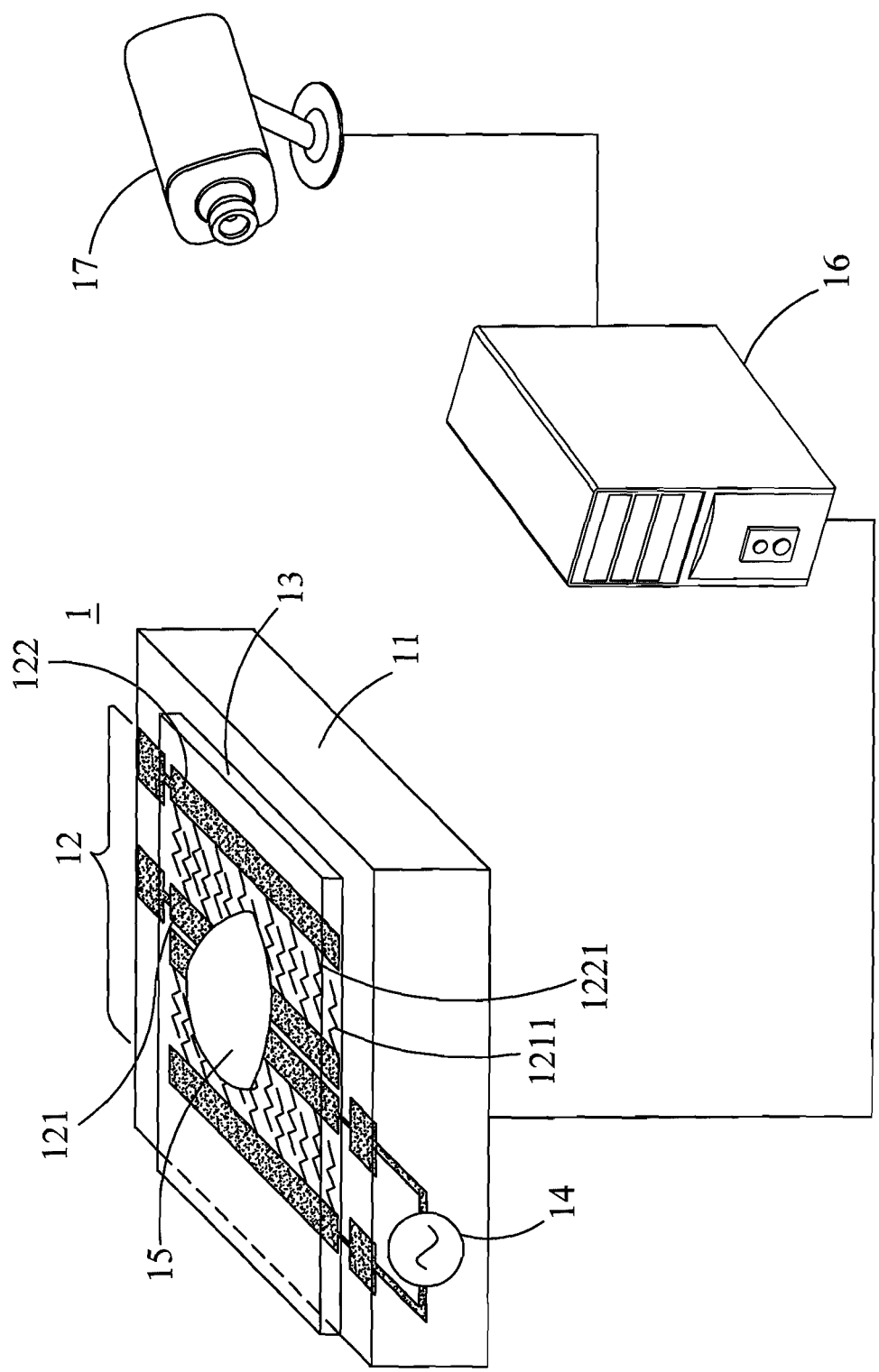
FIG. 1 is a schematic view of a biological detection device in accordance with a first preferred embodiment of the present invention.

With reference to FIG. 1 for a schematic view of a biological detection device in accordance with the first preferred embodiment of the present invention, the biological detection device 1 comprises a substrate 11, an electric field unit 12, a liquid crystal/polymer composite film 13, a power supply 14, a processing unit 16 and an image sensor 17.

The substrate 11 includes but is not limited to a glass substrate. The electric field unit 12 comprises a plurality of electrode pairs, and each electrode pair is installed in parallel with each other on the substrate 11, wherein each electrode pair is consisted of a first strip electrode 121 and a second strip electrode 122, and the first strip electrode 121 has a plurality of first extensions 1211, and each first extension 1211 is arranged with a gap from the other. The second strip electrode 122 has a plurality of second extensions 1221, and each second extension 1221 is arranged with a gap from the other, and each second extension 1221 and each first extension 1211 are arranged alternately with one another. Wherein, each electrode pair can be indium tin oxide (ITO) electrodes. However, the invention is not limited to ITO electrodes only, and electrodes made of any conductive material can be used instead. Wherein, the first extension 1211 and the second extension 1221 are in a sawtooth shape or are linear, but the invention is not limited to these shapes only. The first strip electrode 121 or the second strip electrode 122 has a width falling within a range of 0.1-300 μm, and this preferred embodiment adopts the length of 100 μm. The liquid crystal/polymer composite film 13 has a thickness smaller than 12 μm, and this preferred embodiment adopts the thickness of 6 μm. The liquid crystal/polymer composite film 13 has a root mean square roughness falling within a range of 10~30 nm, and this preferred embodiment adopts 30 nm. The design, thickness and roughness of the electrodes are not limited to those used in the embodiments, they can be changed as needed.

The liquid crystal/polymer composite film 13 is set on the electric field unit 12, and the liquid crystal/polymer composite film 13 includes a liquid crystal director and a macromolecular polymer, and the test sample 15 is set on the liquid crystal/polymer composite film 13, wherein the test sample 15 can be sperm, blood or other biological specimen, and this preferred embodiment adopts serum solution of triglyceride (TG) as the detected test sample, but the invention is not limited to this test sample only.

The power supply 14 is coupled to the electric field unit 12 to provide an in-plane switching electric field to the plurality of electrode pairs, and the electric field is used to change the orientation of the liquid crystal director, so as to change the hydrophilic and hydrophobic properties of the liquid crystal/polymer composite film 13 and drive the test sample 15 to move. Wherein, a voltage value, an AC frequency, and a voltage applying cycle of the power supply 14 can be adjusted according to actual requirements. Further, the power supply 14 is used to provide a periodical pulse voltage to overcome the sluggish movement of the droplet in order to make the motion smoother and the analysis easier.

The processing unit 16 is coupled to the power supply 14, and this preferred embodiment adopts a computer as the processing unit 16 to control the power supply 14 to supply a voltage to the electric field unit 12. However, the processing unit 16 of the invention is not limited to a computer only.

The image sensor 17 is coupled to the processing unit 16, and this preferred embodiment adopts a high-speed CCD camera as the image sensor 17 to capture the test sample 15 on a surface of the liquid crystal/polymer composite film 13 and generates image data of a hydrophilic/hydrophobic motion caused by a change of the electric field, and the image data is provided to the processing unit 16. The processing unit 16 receives the image data, and analyzes a biological property of the test sample according to the image data.

Figure 2:
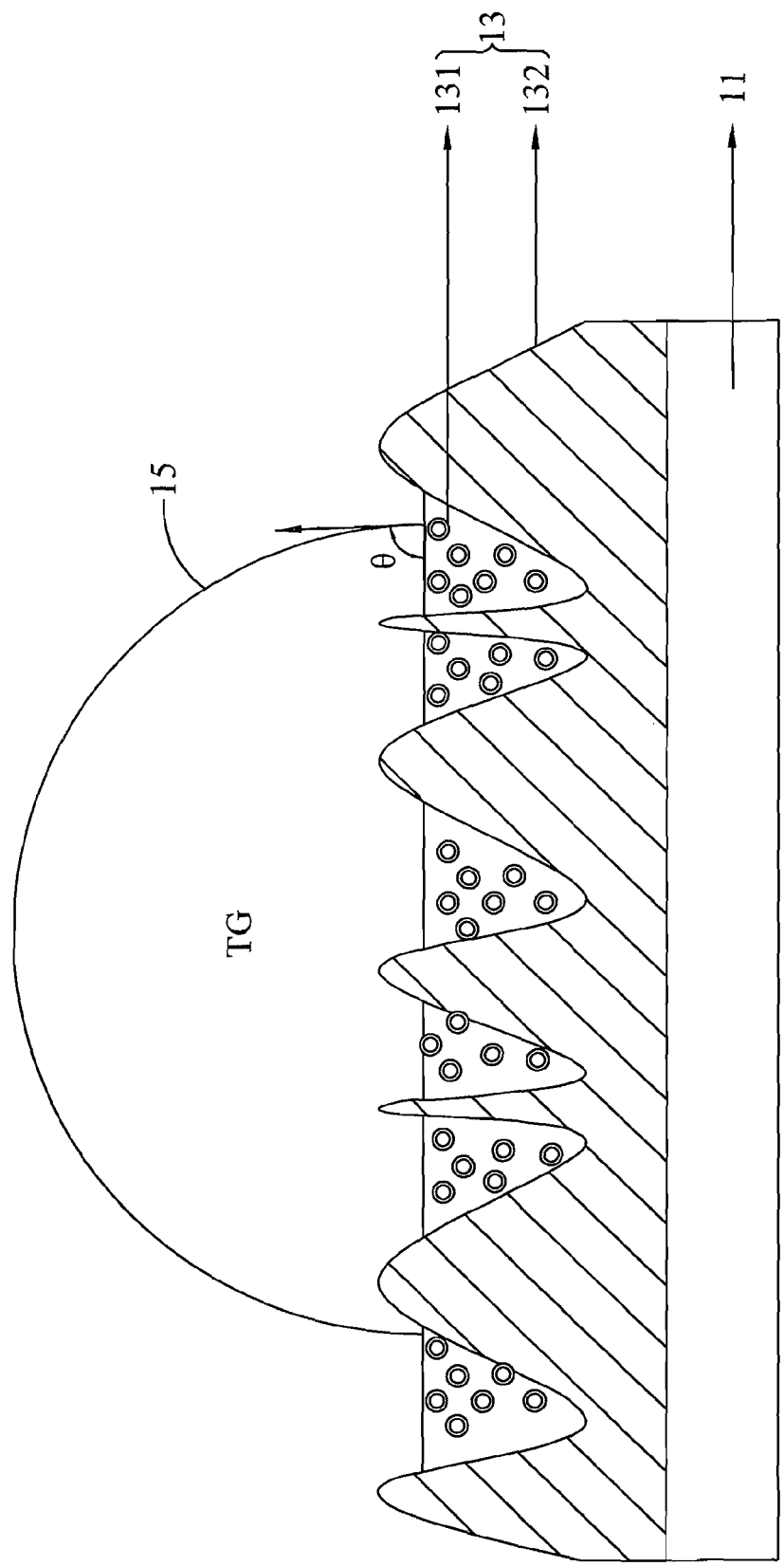
FIG. 2 is a cross-sectional view of a biological detection device in accordance with the first preferred embodiment of the present invention when a voltage is not applied.

With reference to FIG. 2 for a cross-sectional view of a biological detection device in accordance with the first preferred embodiment of the present invention when a voltage is not applied, the biological detection device 1 adopts a glass substrate 11 installed at the bottom of the biological detection device 1 and is coated with a plurality of electrode pairs. The present invention adopts ITO electrodes, and each electrode is configured as shown in FIG. 1 to provide an additional electric field to the liquid crystal director 131. A liquid crystal polymer film 13 comprised of a liquid crystal director 131 and a macromolecular polymer 132 is set on an upper layer of the glass substrate 11, and a test sample 15 to be tested is placed on the top layer, wherein the test sample 15 is a serum droplet containing triglyceride (TG). When the voltage is not applied, the structure of the liquid crystal director 131 is as shown in FIG. 2. The orientation of functional groups in each liquid crystal director 131 remains unchanged, and the droplet of the test sample 15 and the liquid crystal polymer film 13 having a contact angle θ.

Figure 3:
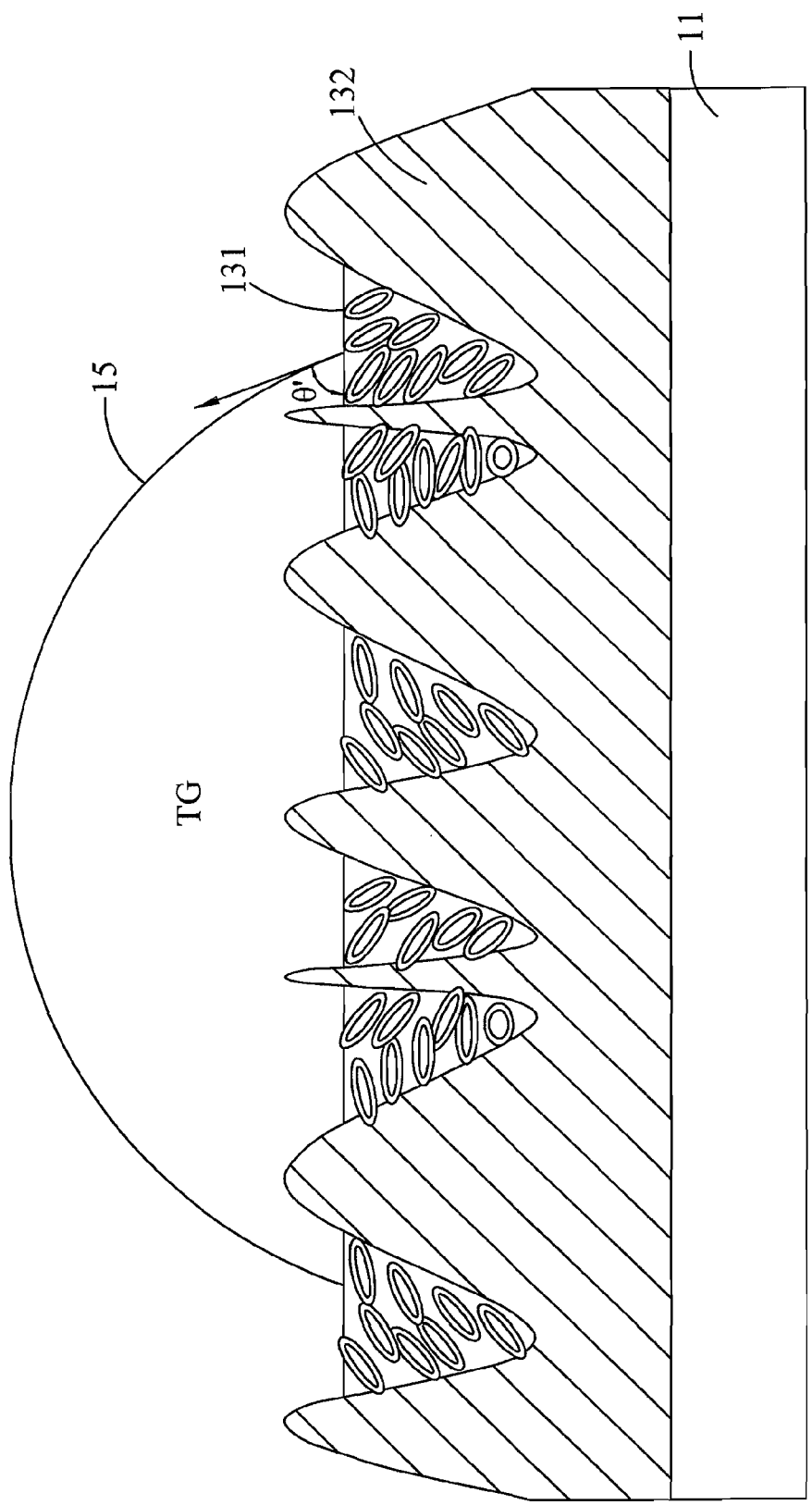
FIG. 3 is a cross-sectional view of a biological detection device in accordance with the first preferred embodiment of the present invention when a voltage is applied.

With reference to FIG. 3 for a cross-sectional view of a biological detection device in accordance with the first preferred embodiment of the present invention when a voltage is applied, the applied voltage generates a parallel electric field, so that the liquid crystal director 131 is rotated, and the orientation of the internal functional groups has a significant change, and the contact angle θ between the droplet of the test sample 15 and the liquid crystal polymer film 13 becomes θ'.

Figure 4:
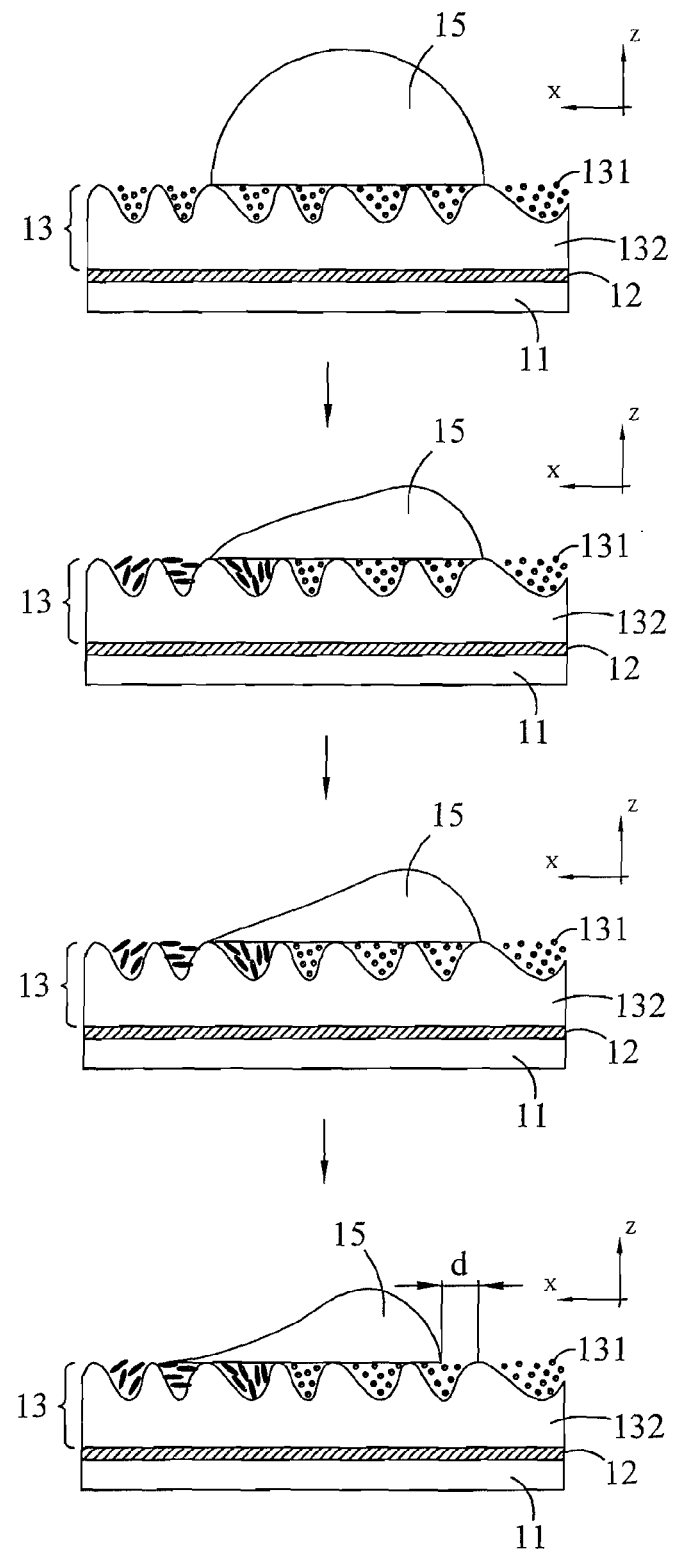
FIG. 4 is a schematic view, showing the hydrophilic property of a surface of a liquid crystal/polymer composite film of the present invention.

With reference to FIG. 4 for a schematic view, showing the hydrophilic property of a surface of a liquid crystal/polymer composite film of the present invention, the orientation of the internal structure of the liquid crystal director 131 has a significant change due to the effect of the electric field. More specifically, the first drawing from the top of FIG. 4 shows the configuration of the test sample 15 is a serum droplet containing triglyceride (TG) when no voltage is applied, wherein the liquid crystal/polymer composite film 13 comprises a liquid crystal director 131 and a macromolecular polymer 132 mixed with each other by concentrations (or weight percentages) in a ratio of 7:3. However, the invention is not limited to the ratio 7:3 only, but the ratios of 5:5, 6:4 or 8:2 can be used instead. The liquid crystal director 131 can be a positive nematic liquid crystal supplied by Merck with the model number E7. The macromolecular polymer 132 is made of organic or inorganic liquid crystalline monomers, and this preferred embodiment adopts a liquid crystalline monomer: 4-(3-Acryloyloxypropyloxy)-benzoic acid 2-methyl-1,4-phenylene ester) supplied by Merck with the module number RM257. The liquid crystal director 131 and the macromolecular polymer 132 are not limited to the foregoing embodiments only, they can be adjusted according to actual requirements.

The second to fourth drawings from the top of FIG. 4 show the configurations of the serum droplet containing triglyceride (TG) when different voltages are applied respectively, and the right half of the drawings 2 to 4 in FIG. 4 shows the orientation of the liquid crystal director 131 in Y-axis (which is parallel to the alignment direction of the substrate during the manufacturing process) when no voltage is applied (V=0). Now, the benzene ring structure of the liquid crystal director 131 is relatively parallel to the thin film surface (Plane x-y), so that the surface of the liquid crystal/polymer composite film 13 is relatively hydrophobic. The left half of the drawings 2 to 4 of FIG. 4 shows that the orientation of the liquid crystal director 131 is changed to the direction of the electric field when an AC voltage (with a frequency 1 KHz) is applied. Now, the boundary effect of the electric field causes the orientation of some liquid crystal directors 131 to change to a cyano terminal group which is closer to the surface of the liquid crystal/polymer composite film 13, so that the surface of the liquid crystal/polymer composite film 13 has a relatively hydrophilic property. Further, the magnitude of the applied voltage value can be changed to control the hydrophilic/hydrophobic property of the surface of the liquid crystal/polymer composite film 13, and users can adjust and control the voltage value according to the actual requirements.

The hydrophilic and hydrophobic properties of the surface of the liquid crystal/polymer composite film 13 are used to control the movement of the droplet of the test sample 15. When no voltage is applied, the left and right contact angles of the droplet of the test sample 15 are equal, and the droplet does not move (as shown in the first drawing from the top of FIG. 4).

If a voltage is applied to the left region, the contact angle on the left of the droplet of the test sample 15 is changed, and the left and right contact angles are no longer equal to produce an unbalanced Young's force, so that the droplet of the test sample 15 moves to the left to produce a moving distance d, while producing a collapse speed to move the triglyceride droplet to a small distance (moving distance) as shown in the second to fourth drawings from the top of FIG. 4.

In FIGS. 1 and 4, the test sample 15 in a liquid form to be tested is placed in the middle between two strip electrode regions, and an end of the test sample 15 is in contact with another strip electrode (wherein the contact point shown in the figure is situated on the left side of the droplet of the test sample 15 to be tested. When a periodical pulse voltage is outputted at each ITO electrode pair, the voltage is applied to one of the electrode regions (which is the left electrode region) only as shown in FIG. 1, since the droplet of the test sample 15 to be tested is situated across two electrode regions. No voltage is applied to the right electrode region as shown in FIG. 4. The liquid crystal director 131 on the left will be rotated along the electric field because of the electric field that is applied and the liquid crystal director 131 on the right will not be rotated and is still arranged in the alignment direction of the time of manufacture. Now, the benzene structure of the liquid crystal director 131 is parallel to the thin film surface, and the surface has a very low polarity. However, the liquid crystal director 131 of the left electrode region will be rotated due to the electric field, and the long-chain terminal of the liquid crystal director 131 tends to turn along the electric field and towards the surface, and the cyano terminal group of the liquid crystal director 131 have molecules with a stronger polarity, so that the polarity of the left surface is considered to have become stronger. Since the test sample 15 is disposed across two testing electrode regions with unequal polarities, therefore the test sample 15 will be attracted to the stronger polarity and collapse, and the left and right contact angles will be unequal. As a result, an unbalanced Young's force is produced, and the test sample 15 tends to move to the left. The concentration of the triglyceride can be determined according to the change of the measured contact angles or the motion of the serum droplet containing triglyceride.

The manufacturing process of the liquid crystal/polymer composite film of the present invention is described as follows. Firstly, a positive nematic liquid crystal (nematic liquid crystal mixture: Model No. E7 by Merck) and a liquid crystalline monomer: 4-(3-Acryloyloxypropyloxy)-benzoic acid 2-methyl-1,4-phenylene ester) are mixed with a concentration ratio (in terms of weight percentages) of 7:3. The positive nematic liquid crystal and the liquid crystalline monomer are filled into a hollow liquid crystal cell. The liquid crystal cell has a gap thickness of 6 nm and includes an upper substrate and a lower substrate, and the lower glass substrate is coated with a sawtooth ITO electrode, and the upper glass substrate is coated with a liquid crystal alignment layer whose alignment direction has an included angle of 15 degrees with respect to the strip electrode. UV is projected for 50 min (UV intensity is equal to 10 mW/cm$^2$) after the mixture is filled and after the phase separation and photo-polarization is completed, the upper glass substrate is peeled and removed, so that the liquid crystal/polymer composite film is produced. The liquid crystal/polymer composite film has a thickness of 6 μm and a root-mean-squared roughness of 30 nm.

Figure 5:
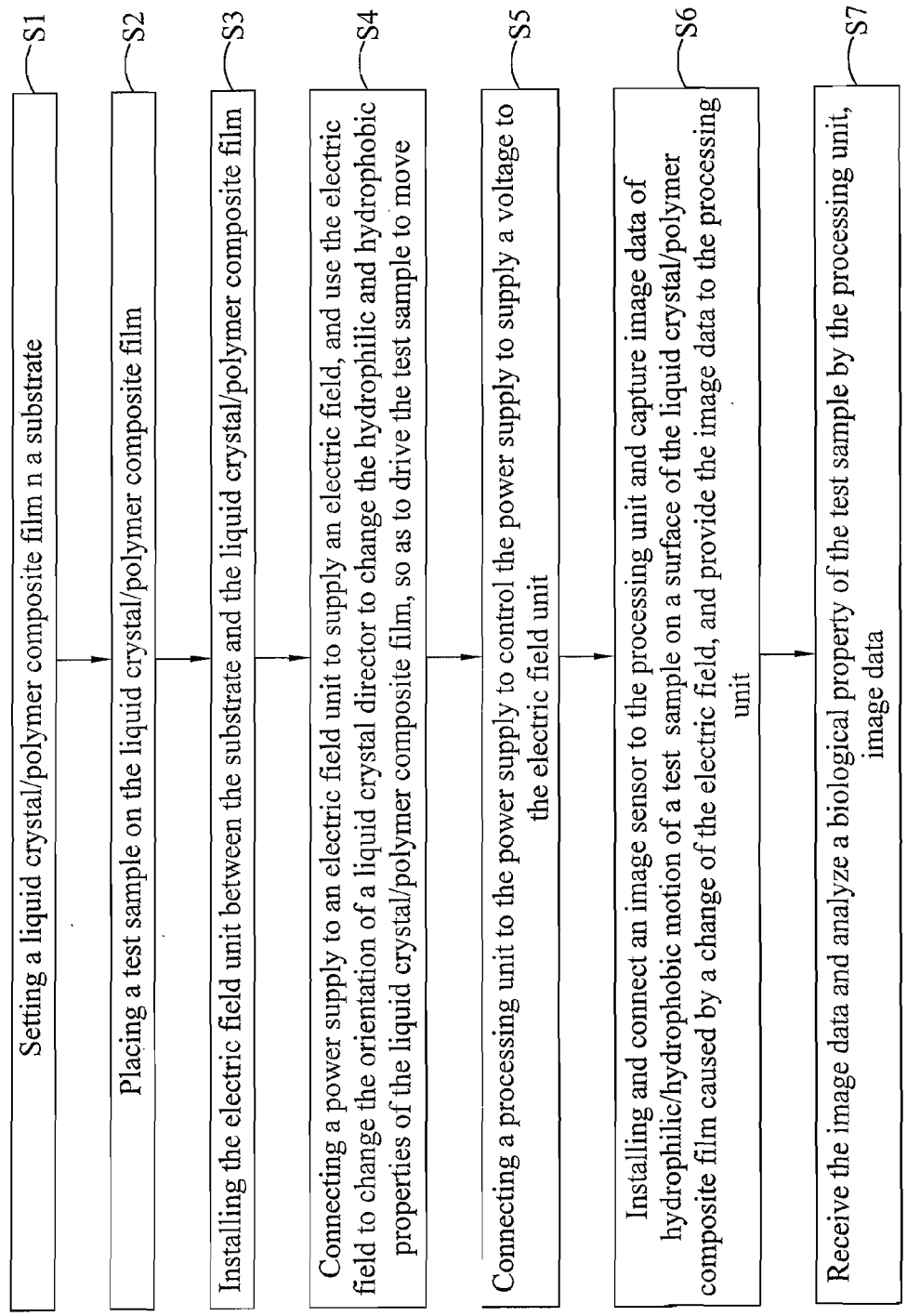
FIG. 5 is a flow chart of a detecting method of a biological detection device of the present invention.

With reference to FIG. 5 for a flow chart of a detecting method of a biological detection device of the present invention and FIG. 1 for the schematic view of a biological detection device, the detecting method comprises the following steps:

S1: Setting a liquid crystal/polymer composite film (LCPCF) on a substrate.

S2: Placing a test sample on the liquid crystal/polymer composite film.

S3: Installing the electric field unit between the substrate and the liquid crystal/polymer composite film.

S4: Connecting a power supply to an electric field unit to supply an electric field, and use the electric field to change the orientation of a liquid crystal director to change the hydrophilic and hydrophobic properties of the liquid crystal/polymer composite film, so as to drive the test sample to move.

S5: Connecting a processing unit to the power supply to control the power supply to supply a voltage to the electric field unit.

S6: Installing and connect an image sensor to the processing unit and capture image data of hydrophilic/hydrophobic motion of a test sample on a surface of the liquid crystal/polymer composite film caused by a change of the electric field, and provide the image data to the processing unit.

S7: Receiving the image data and analyze a biological property of the test sample by the processing unit, image data, wherein the image data can be a database of contact angle, moving distance or collapse speed captured by the image sensor, but the invention is not limited to these databases only.

Figure 6:
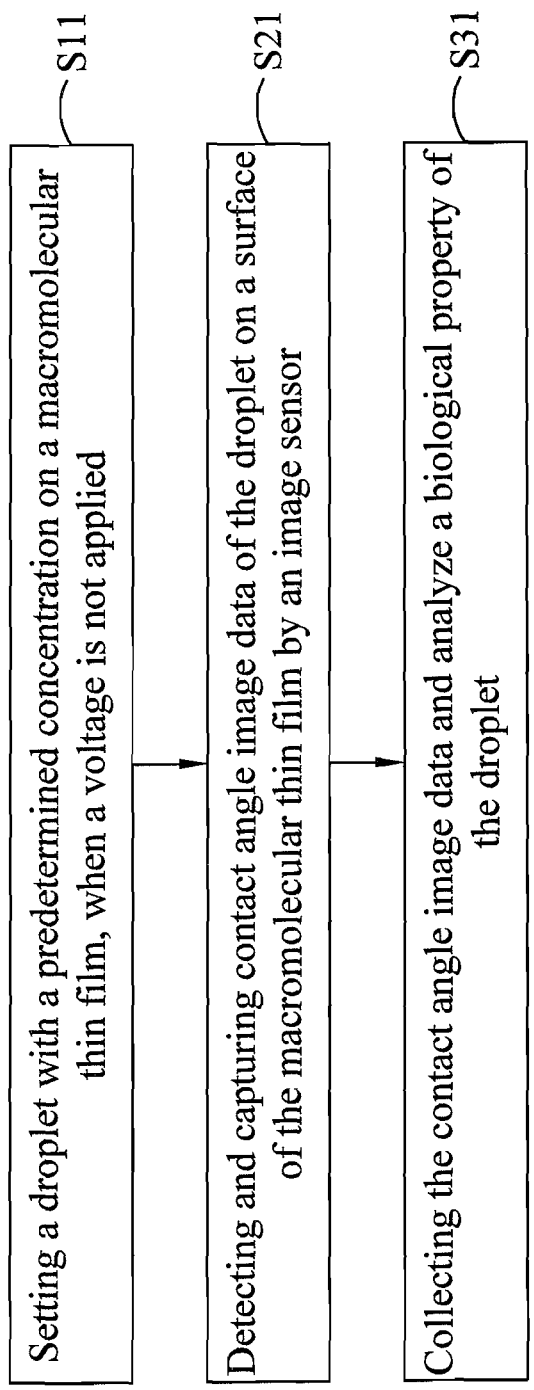
FIG. 6 is a flow chart of a detecting method of a biological detection device of the present invention when a voltage is not applied.

With reference to FIG. 6 for a flow chart of a detecting method of a biological detection device in accordance with the present invention when no voltage is applied, the detecting method comprises the following steps:

S11: Setting a droplet with a predetermined concentration on a macromolecular thin film, when a voltage is not applied.

S21: Detecting and capturing contact angle image data of the droplet on a surface of the macromolecular thin film by an image sensor.

S31: Collecting the contact angle image data and analyze a biological property of the droplet, wherein the image data can be a database of contact angle, moving distance or collapse speed captured by the image sensor, but the invention is not limited to these databases only.

Second Preferred Embodiment

In this preferred embodiment, the test sample is a serum solution obtained from a hospital. The biological detection device and the detecting method of the present invention perform a detection and analysis when a voltage is applied or when no voltage is applied.

Firstly, a serum solution is obtained from a hospital, and the serum solution is set aside to cool to room temperature, and then a test tube containing the serum solution is shaken slightly and uniformly, and a dropper is used to place the serum solution on a liquid crystal/polymer composite film (LCPCF), and the liquid crystal/polymer composite film is put onto an observation table. A high-speed CCD camera is installed to the side to record the condition of the serum droplet and transmit the data to a computer, and a computer program FTA32 is provided for identification and analysis. The high-speed CCD camera (Model No. CVM30, CCD, by Pentad) takes the photo of a contact angle of the observed serum droplet on the liquid crystal/polymer composite film. (No voltage is applied during the aforementioned detection process).

And then, an electrode rod is placed on an electrode substrate under the liquid crystal/polymer composite film and a voltage of 200V is applied to generate an electric field to drive the liquid crystal director to rotate and cause a change of the hydrophilic and hydrophobic properties of the surface of the liquid crystal/polymer composite film. Now, the high-speed CCD camera installed to the side takes the photo of the movement of the observed serum solution and transmits the data to the computer for further analyses. (Wherein a voltage is applied during the aforementioned detection process).

Figure 7A:
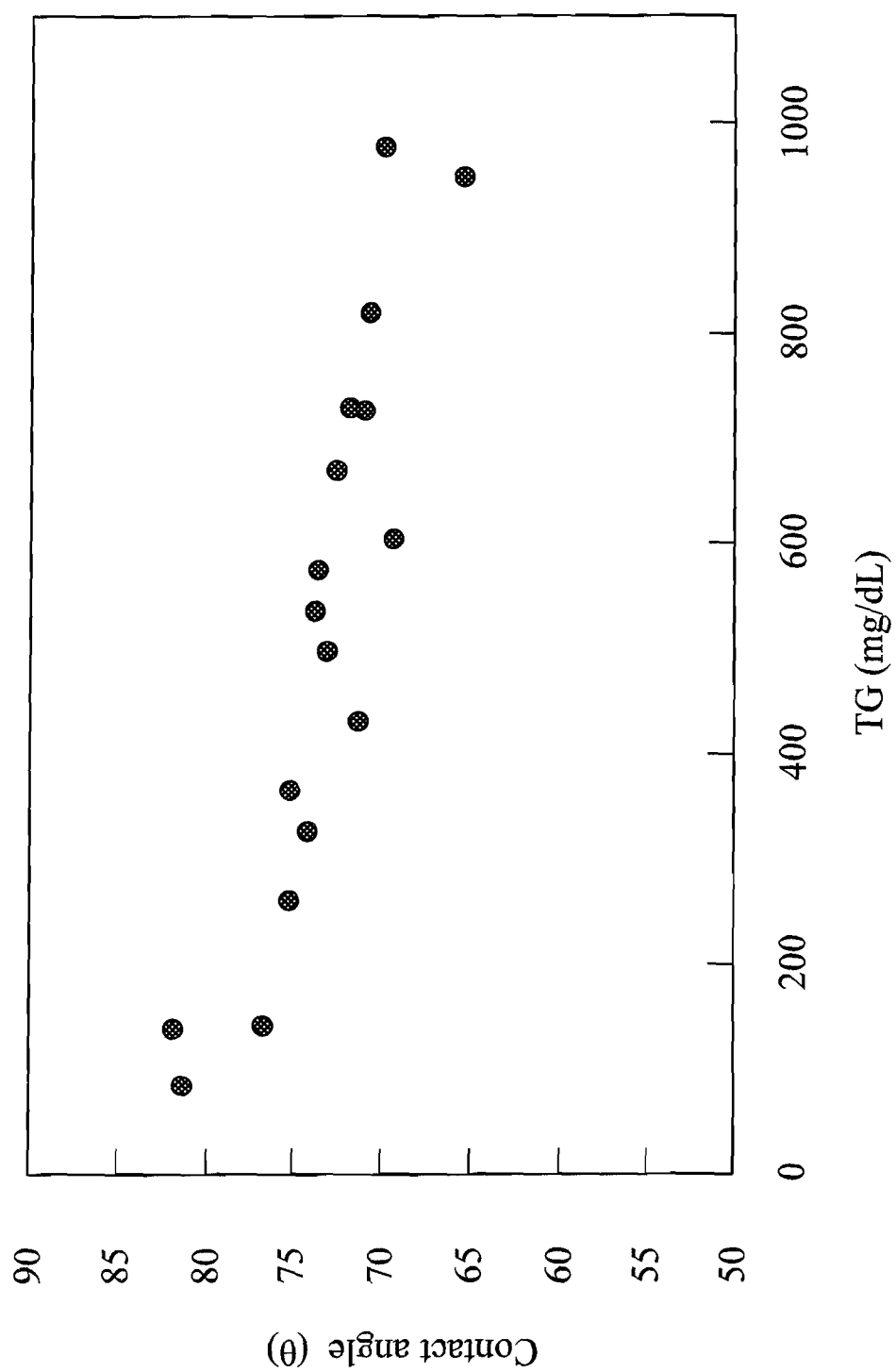
FIG. 7A is a graph showing data of a contact angle obtained from detecting triglyceride in a blood droplet by a biological detection device of the present invention when a voltage is not applied.
Figure 7B:
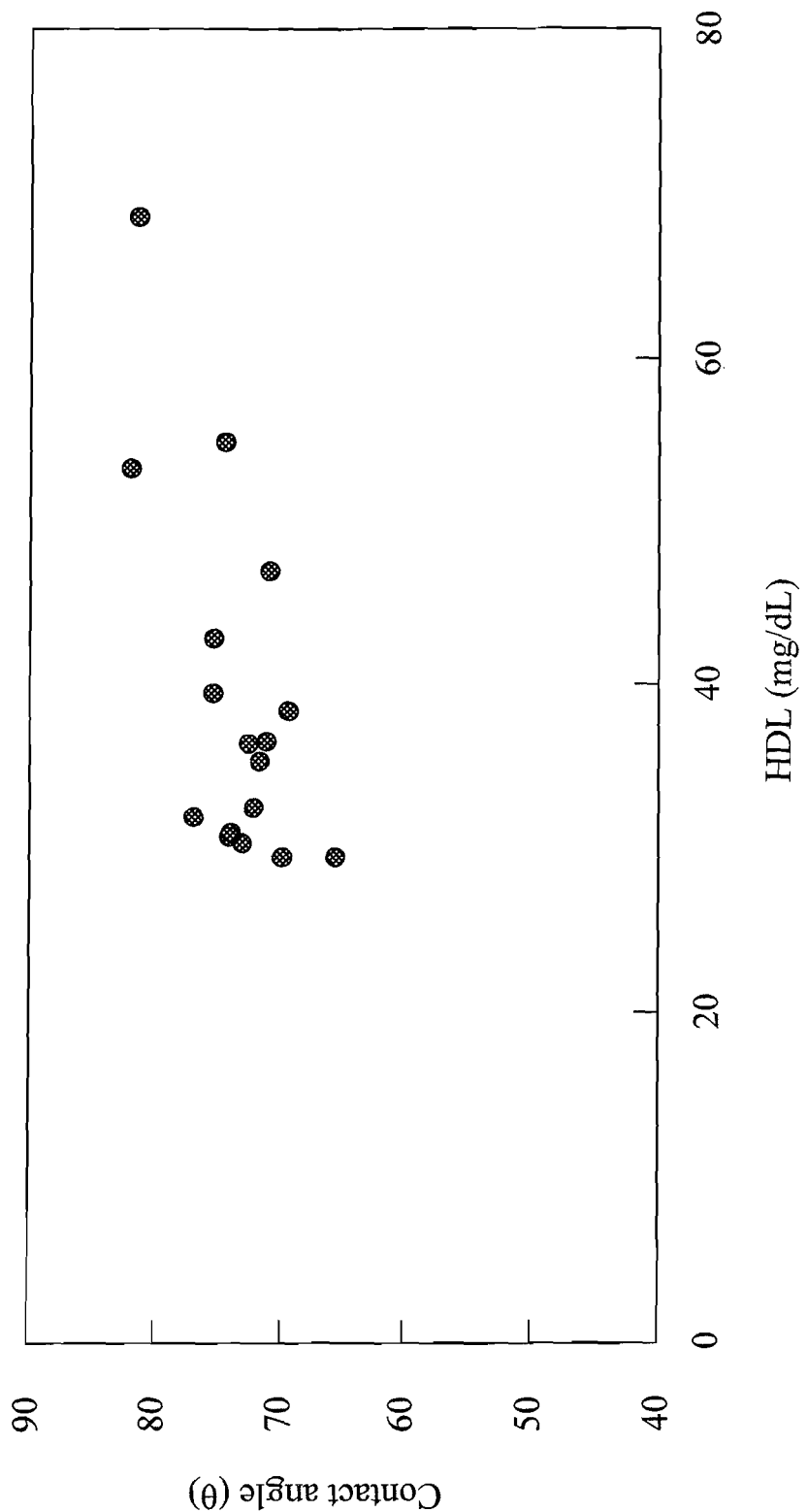
FIG. 7B is a graph showing data of a contact angle obtained from detecting high density liposome in a blood droplet by a biological detection device of the present invention when a voltage is not applied.
Figure 7C:
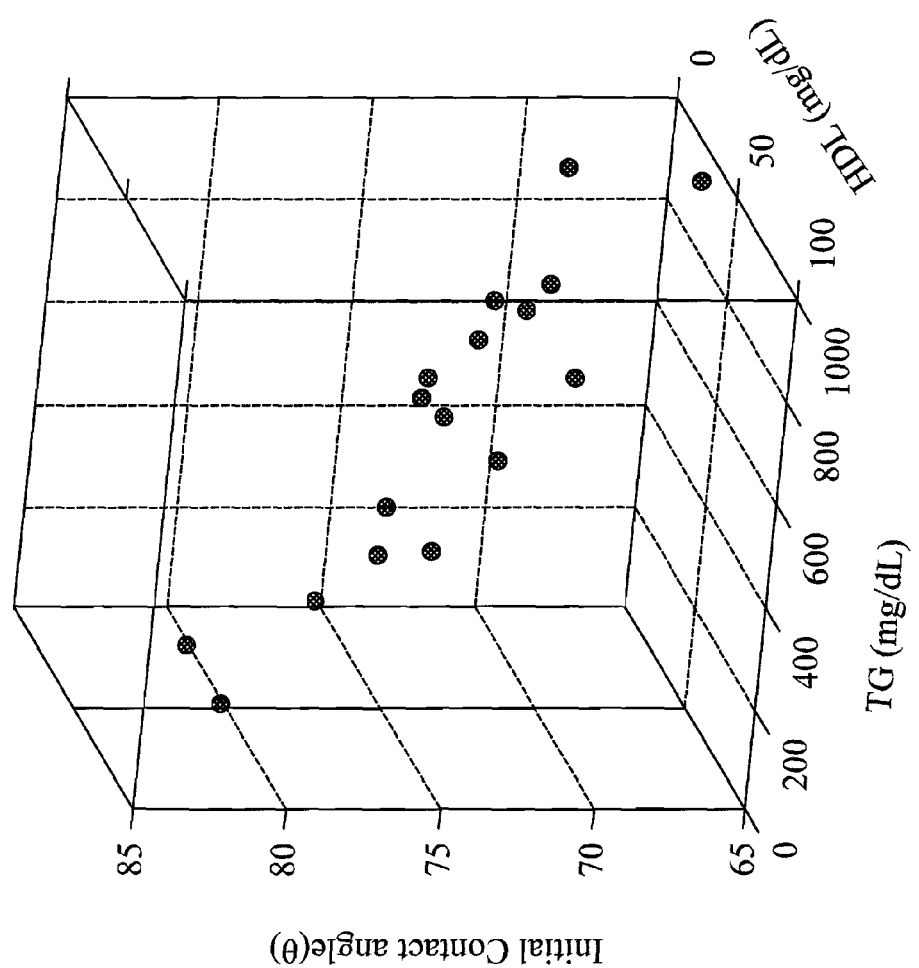
FIG. 7C is a 3D perspective view showing computer simulated, computed and analyzed data of triglyceride, high density liposome, and contact angle of the present invention.

With reference to FIGS. 7A~7C, FIG. 7A shows the result of a contact angle obtained from detecting triglyceride in a serum droplet on a liquid crystal polymer film by a biological detection device of the present invention when a voltage is not applied. The contact angle data of the serum droplet detected by the high-speed CCD camera are transmitted to the computer and a biological property of the serum droplet is analyzed. With reference to FIGS. 7A and 7B respectively for graphs showing data of a contact angle obtained from detecting triglyceride (TG) and high density liposome (HDL) in serum droplets of different concentrations by a biological detection device of the present invention when a voltage is not applied, the contact angle of the serum droplet varies in accordance with the TG and HDL concentration levels. The greater the TG concentration and the smaller the HDL concentration, the higher is the polarity of the serum and the smaller is the volume of the HDL and are replaced with large composite molecules such as chylomicrons or very low density liposome (VLDL), so that the polarity of the serum droplet will rise. As to the liquid crystal polymer film with no voltage applied, the surface of this polymer film has no polarity, so that when a voltage is applied to the liquid crystal polymer film, its polarity will drop, and the interface attraction between the surface of the serum droplet and the liquid crystal polymer film will increase, and the serum droplet will display a low contact angle as the TG concentration become increasingly higher or as the HDL concentration become increasingly lower. In the linear regression formula as shown in FIG. 7A, (T)=−0.01283T+79.99, wherein ($\Theta$) is the contact angle, and T is the TG concentration. In the linear regression formula as shown in FIG. 7B, (H)=0.2397H+63.84, wherein ($\Theta$) is the contact angle, and H is the HDL concentration. The results of the TG concentration versus the contact angle can be used to compare with the TG concentration defined by hospitals to create Table 1. The TG concentration is considered to have a normal value if the TG concentration is below 150 mg/dl and the contact angle is above 78 degrees. The TG concentration is considered to have a marginally high value if the TG concentration falls within a range of 150 mg/dl~200 mg/dl, and the contact angle is approximately equal to 77~78 degrees. The TG concentration is considered to have a high value if the TO concentration falls within a range from 200 mg/dl to 499 mg/dl, and the contact angle is approximately equal to 73~77 degrees. The TG concentration is considered to have a very high value if the TG concentration is greater than 500 mg/dl, and the contact angle is smaller than 73 degrees.

TABLE 1

| Item | Normal Value | Marginally High Value | High Value | Very High Value |
|---|---|---|---|---|
| TG concentration (mg/dL) | <150 | 150-199 | 200-499 | ≥500 |
| TG contact angle (deg) | >78 | 77~78 | 73~77 | <73 |

From the above results, we can inspect the serum droplet to evaluate the range of the examinee's triglyceride concentration. If the initial contact angle is greater than 78 degrees, then a normal value is obtained, but if the contact angle is smaller than 77 degrees, then the subject has to pay more attention to health and exercise control on the diet. If the contact angle falls below 73 degrees, the subject has a relatively serious problem with a high lipid concentration and requires medical assistance. The HDL and the contact angle of the serum are directly proportional to each other. The higher the HDL concentration, the greater is the contact angle of the serum. In other words, the subject has a smaller risk of hyperlipidemia if a larger contact angle is measured.

FIG. 7C shows the biological information of contact angles of the combined triglyceride (TG) and high density liposome (HDL) as depicted in FIGS. 7A and 7B, and FIG. 7C also shows the following linear regression formula:

$$\theta(T,H)=74.9-0.0092 \times T+0.135 \times H+3.201 \times 10^{-6} \times T^2 - 0.0001473 \times T \times H - 0.0002654 \times H^2$$

wherein, $\theta$ is the contact angle; H is the HDL concentration; and T is the TG concentration. Computer simulated computation and analysis are performed to obtain a 3D perspective diagram showing a change of contact angle of the serum droplet on the liquid crystal polymer film. A processing unit (or computer) is provided and connected to an image sensor (or a high-speed CCD camera) to obtain the image data, and the computer simulated computation can be used to obtain a biological information analysis result quickly, and thus saving time and laboratory costs, the computer can also be used to predict possible experiment results such as the prediction of unknown concentrations of triglyceride and high density liposome, the detected image data can be inputted into present existing databases, and an interpolation method is used to simulate, predict and analyze the concentration of the test sample.

The biological detecting method of the present invention improves over the conventional blood analysis method successfully and uses a simple and quick detecting method to examine the concentration of triglyceride and high density liposome, so that users can know more about their own health information and also of their family.

Figure 8A:
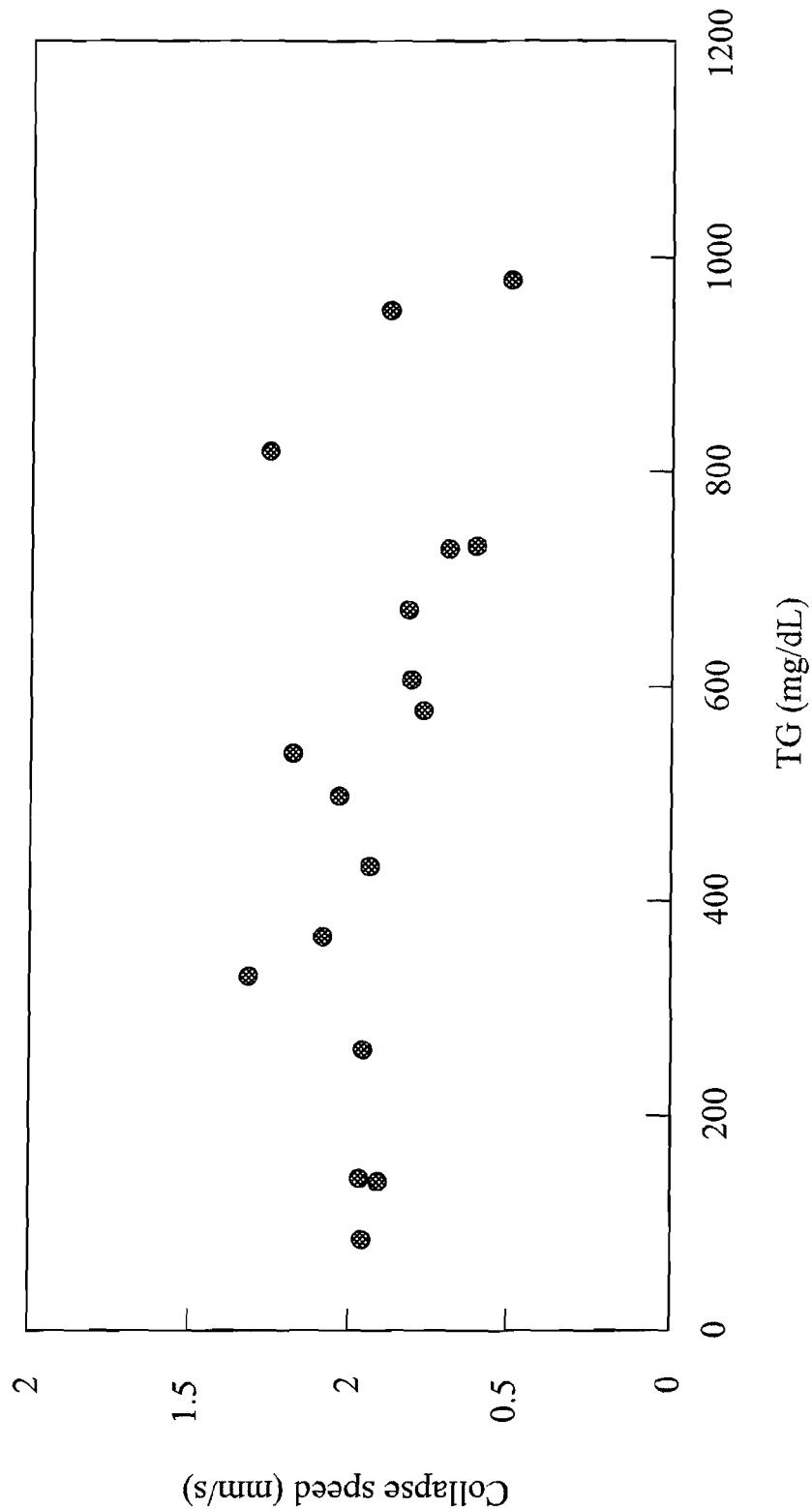
FIG. 8A is a graph of data of collapse speed obtained from detecting triglyceride droplets by a biological detection device of the present invention when a voltage is applied.
Figure 8B:
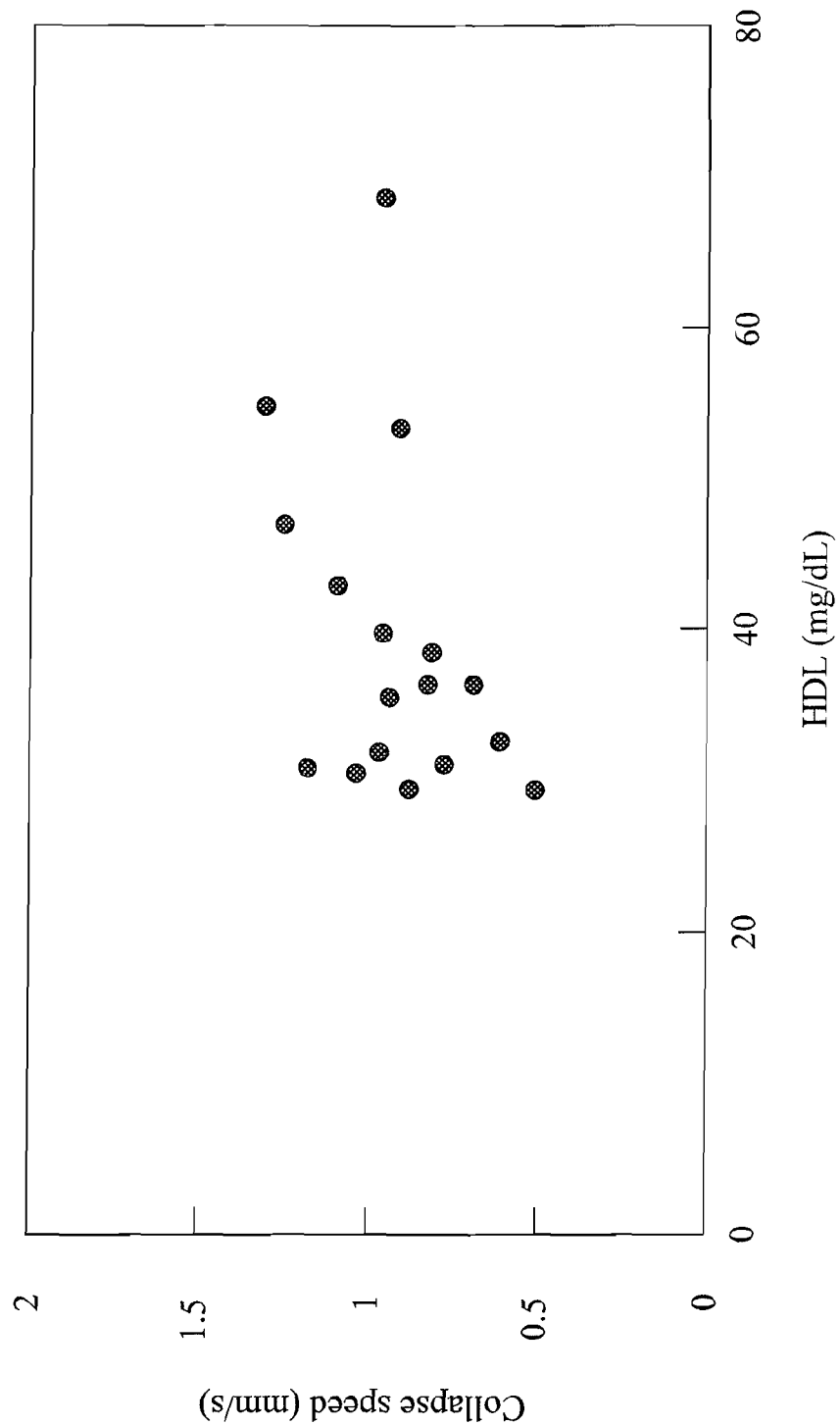
FIG. 8B is a graph of data of collapse speed obtained from detecting high density liposome droplets by a biological detection device of the present invention when a voltage is applied.
Figure 8C:
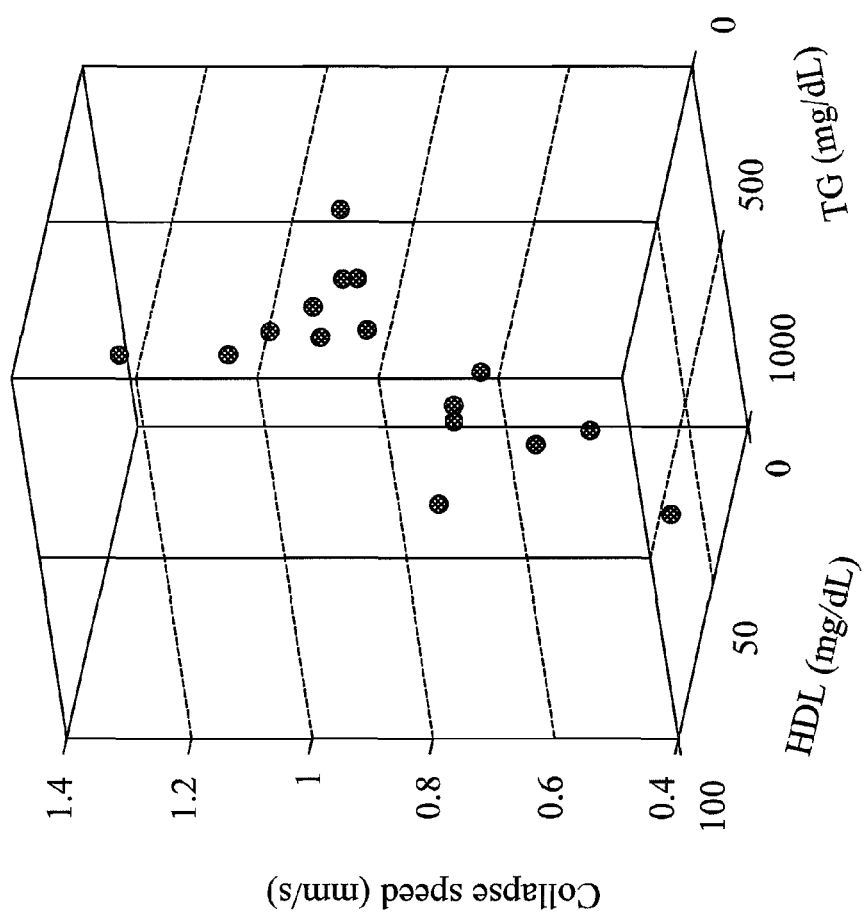
FIG. 8C is a 3D perspective view showing computer simulated, computed and analyzed data of triglyceride, high density liposome, and collapse speed of the present invention.

With reference to FIGS. 8A~8C for results of a change of serum droplet on a liquid crystal polymer film when a voltage is applied, a voltage is applied to a triglyceride droplet in this preferred embodiment to produce a change of contact angle, and the applied voltage causes unequal left and right intersecting angles of the triglyceride droplet, so that the portion of the droplet with the applied voltage is collapsed to produce a collapse speed, so that the triglyceride droplet can move in a small distance (which is the moving distance). The high-speed CCD camera is used for detecting the collapse speed and moving distance of the serum droplet, and the data are transmitted to the computer to analyze the biological property of the serum droplet. With reference to FIGS. 8A and 8B respectively for graphs of data of the collapse speed obtained from detecting triglyceride (TG) and high density liposome (HDL) droplets by a biological detection device of the present invention when a voltage is applied, a serum droplet with a higher TG concentration and a lower HDL concentration has a lower polarity. The stronger the polarity of the electrically controlled surface polarity of the liquid crystal polymer film, the weaker is the attraction force, and the lower is the collapse speed. As a result, the movement is more difficult, and the moving distance is shorter. With reference to FIG. 8C and the biological information including the collapse speeds of the triglyceride and high density liposome as shown in FIGS. 8A and 8B, computer simulated computation and analysis are conducted and the results are used to draw a 3D perspective diagram of the change of collapse speed of the serum droplet on the liquid crystal polymer film.

Figure 9A:
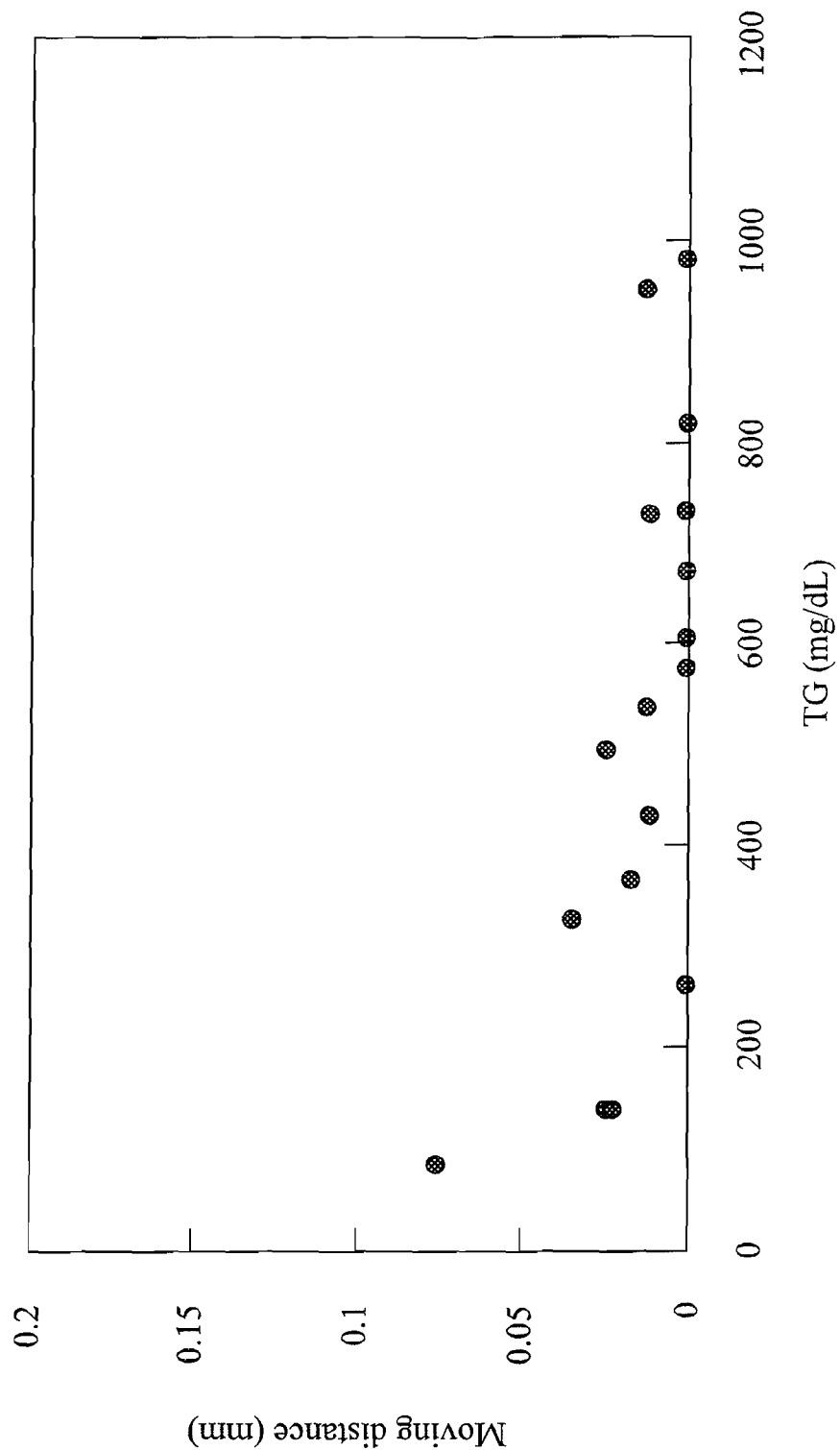
FIG. 9A is a graph of data of moving distance obtained from detecting triglyceride droplets by a biological detection device of the present invention when a voltage is applied.
Figure 9B:
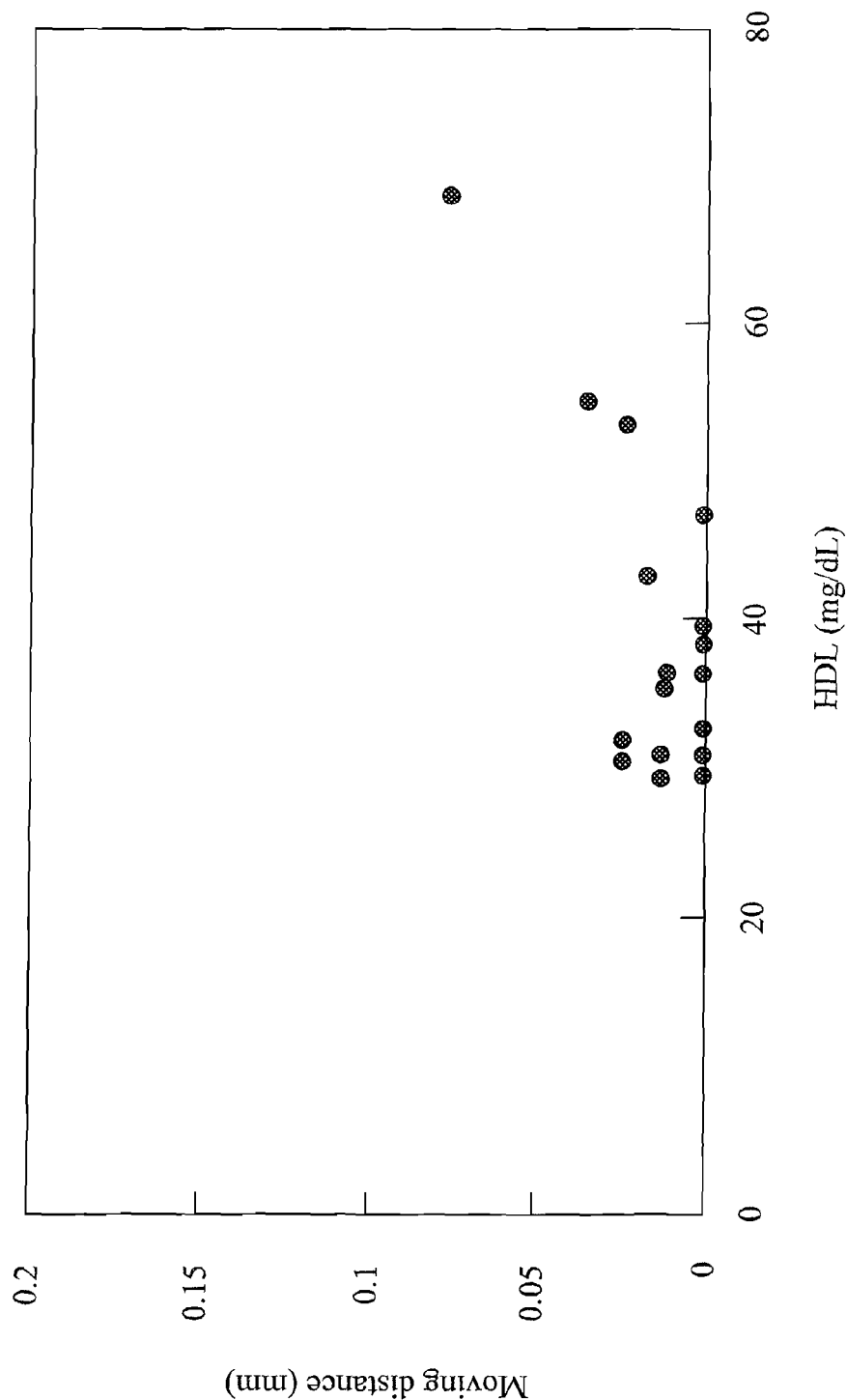
FIG. 9B is a graph of data of moving distance obtained from detecting high density liposome by a biological detection device of the present invention when a voltage is applied.

With reference to FIGS. 9A and 9B, the movement of the serum on the liquid crystal polymer film with the electrically controlled surface polarity is used to detect the TG and HDL.

Figure 9C:
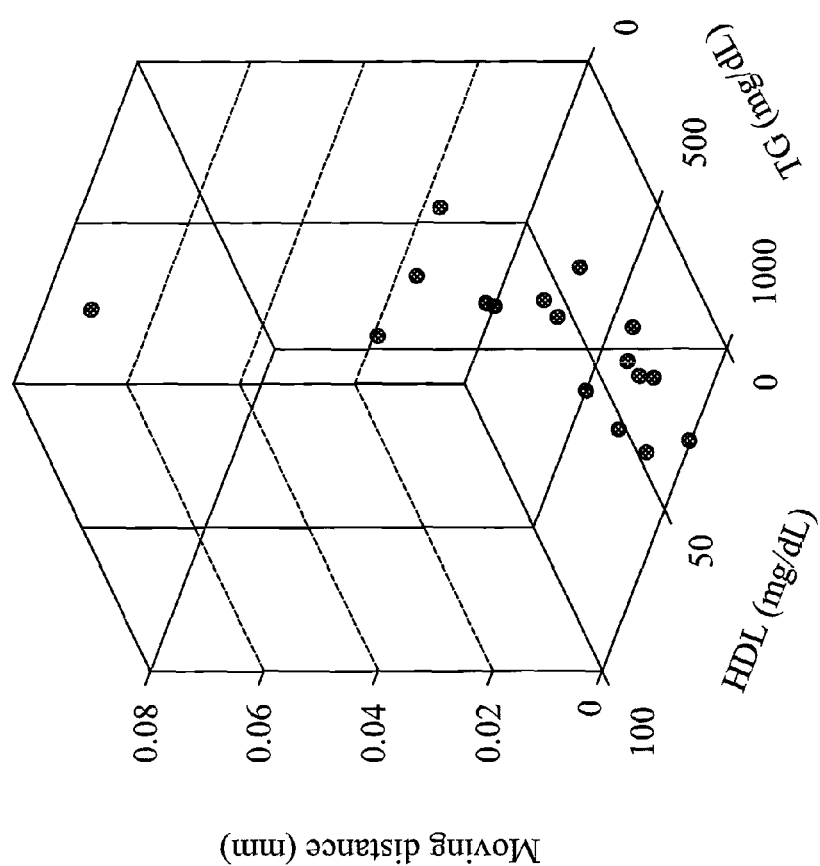
FIG. 9C is a 3D perspective view showing computer simulated, computed and analyzed data of triglyceride, high density liposome, and moving distance of the present invention.

With reference to FIG. 9C is the biological information including the moving distance of the triglyceride and high density liposome as shown in FIGS. 9A and 9B, the computer simulated computation and analysis are conducted and the results are used to draw a 3D perspective diagram of the change of moving distance of the serum droplet on the liquid crystal polymer film.

The results of TG and HDL concentration versus collapse speed are used to compare with the TG and HDL concentration defined by hospitals to compile the following tables 2 and 3. Similarly, the results of TG concentration versus serum moving distance are used to define and create the following table 4.

TABLE 2

| Item | normal value | marginally high value | high value | very high value |
|---|---|---|---|---|
| TG concentration (mg/dL) | 150↓ | 150~200 | 200~500 | 500↑ |
| TG collapse speed (mm/s) | 1.03↑ | 1.03~1.02 | 1.02~0.92 | 0.92↓ |
| TG moving distance (mm) | 0.04↑ | 0.04~0.01 | 0.01~(~0) | (~0) |

TABLE 3

| HDL | Normal Value (over 35 mg/dL) | High Value (over 60 mg/dL) with heart protection effect |
|---|---|---|
| HDL initial contact angle (deg) | 72.23 | 78.22 |
| HDL collapse speed (mm/s) | 0.88 | 1.08 |
| HDL moving distance (mm) | 0.01 | 0.04 |

TABLE 4

| Item | Normal Value | Marginally High Value | High Value | Very High Value |
|---|---|---|---|---|
| TG concentration (mg/dL) | <150 | 150~200 | 200~500 | >500 |
| Serum initial contact angle (deg) | >78 | 77~78 | 73~77 | <73 |
| Serum collapse speed (mm/s) | >0.99 | 0.99~0.97 | 0.97~0.92 | <0.92 |
| Serum moving distance (mm) | >0.02 | 0.02~0.01 | 0.01~0 | 0 |

The biological detection device of the present invention uses a simple and quick method to examination the concentration of triglyceride and high density liposome The present invention improves the long process of analyzing blood quality and allows users to know about the preliminary information of their blood timely and obtain physiological information easily without going through a complicated chemical analysis.

The electrically controlled surface polarity of the liquid crystal/polymer composite film is in contact with the serum, and the observation made by the processing unit and image sensor can be used to obtain and analyze the biological information of the triglyceride and high density liposome and predict the subject's health conditions. The present invention can be applied extensively in the biomedial field including biosensors and micro-fluidic channel, and provides a new business opportunity based on the well-developed LCD industry.

What is claimed is:

1. A biological detection device used to detect a test sample in a liquid form, comprising: a substrate; a liquid crystal/polymer composite film, including a liquid crystal director and a macromolecular polymer, and the test sample being disposed on the liquid crystal/polymer composite film; an electric field unit, installed between the substrate and the liquid crystal/polymer composite film; a power supply, coupled to the electric field unit, for supplying a voltage to form an electric field, and the electric field being used for changing an orientation of the liquid crystal director to change hydrophilic and hydrophobic properties of the liquid crystal/polymer composite film to drive the test sample to move; a processing unit, coupled to the power supply, for controlling the power supply to supply the voltage to the electric field unit; and an image sensor, coupled to the processing unit, for capturing image data of a hydrophilic/hydrophobic motion of the test sample moved on a surface of the liquid crystal/polymer composite film and caused by a change of the electric field, and providing the image data to the processing unit; wherein the processing unit receives the image data, and concurrently analyzes concentrations of triglyceride and high density liposome a biological property of the test sample according to the image data, wherein the processing unit analyzes a change of data of a contact angle, a moving distance or a collapse speed of the test sample in the image data and compares the data with a reference database to determine the concentrations of triglyceride and high density liposome of the test sample; wherein the contact angle is represented by the formula:

$$\theta(T,H)=74.9-0.0092*T+0.135*H+3.201*10^{-6}*T^2-0.0001473*T*H-0.0002654*H^2,$$

wherein $\theta$ is the contact angle, H is the concentration of high density liposome and T is the concentration of triglyceride.

2. The biological detection device of claim 1, wherein the electric field unit comprises a plurality of electrode pairs arranged adjacent and parallel to one another on the substrate, and each electrode pair comprises:
a first strip electrode, including a plurality of first extensions arranged with an interval apart from one another; and
a second strip electrode, including a plurality of second extensions arranged with an interval apart from one another and each second extension and each first extension are arranged alternately.

3. The biological detection device of claim 1, wherein the liquid crystal director is a positive nematic liquid crystal.

4. The biological detection device of claim 1, wherein the macromolecular polymer is made of organic or inorganic liquid crystalline monomers.

5. The biological detection device of claim 1, wherein the liquid crystal director and the macromolecular polymer have a concentration ratio in terms of weight percentage ranging from 5:5 to 8:2.

6. The biological detection device of claim 1, wherein the image sensor is a high-speed CCD camera.

7. A biological detecting method, used for testing a test sample in a liquid form, comprising the steps of: setting a liquid crystal/polymer composite film on a substrate; putting the test sample on the liquid crystal/polymer composite film; installing an electric field unit between the substrate and the liquid crystal/polymer composite film; providing a power supply to be coupled to the electric field unit to provide an electric field, and using the electric field to change an orientation of a liquid crystal director to change hydrophilic and hydrophobic properties of the liquid crystal/polymer composite film to drive the test sample to move; connecting a processing unit to the power supply to control the power supply to supply a voltage of the electric field unit; and connecting an image sensor to the processing unit to capture the test sample on a surface of the liquid crystal/polymer composite film, and generating image data of a hydrophilic/hydrophobic motion caused by a change of the electric field, and providing the image data to the processing unit; wherein the processing unit receives the image data, and concurrently analyzes concentrations of triglyceride and high density liposome a biological property of the test sample according to the image data, wherein the processing unit analyzes a change of data of a contact angle, a moving distance or a collapse speed of the test sample in the image data and compares the data with a reference database to determine the concentrations of triglyceride and high density liposome of the test sample; wherein the contact angle is represented by the formula:

$$\theta(T,H)=74.9-0.0092*T+0.135*H+3.201*10^{-6}*T^2-0.0001473*T*H-0.0002654*H^2,$$

wherein $\theta$ is the contact angle, H is the concentration of high density liposome and T is the concentration of triglyceride.

8. The biological detecting method of claim 7, further comprising the step of mixing a liquid crystal director with a macromolecular polymer with a concentration ratio in terms of weight percentage ranging from 5:5 to 8:2 to form the liquid crystal/polymer composite film.

9. The biological detecting method of claim 7, wherein the image sensor is a high-speed CCD camera.

10. A biological detecting method, used for testing a droplet in a liquid form and a predetermined concentration, comprising the steps of: setting the droplet on a macromolecular thin film, when a voltage is not applied; using an image sensor to detect and capture contact angle image data of the droplet on a surface of the macromolecular thin film; and collecting the contact angle image data and concurrently analyzing concentrations of triglyceride and high density liposome of the droplet according to the contact angle image data, wherein the concentrations of triglyceride and high density liposome of the droplet are determined by analyzing a change of data of a contact angle, a moving distance or a collapse speed of the droplet in the contact angle image data and comparing the data with a reference database; wherein the contact angle is represented by the formula:

$$\theta(T,H)=74.9-0.0092*T+0.135*H+3.201*10^{-6}*T^2-0.0001473*T*H-0.0002654*H^2,$$

wherein $\theta$ is the contact angle, H is the concentration of high density liposome and T is the concentration of triglyceride.

11. The biological detecting method of claim 10, further comprising the step of mixing a liquid crystal director with a macromolecular polymer with a concentration ratio in terms of weight percentage ranging from 5:5 to 8:2 to form the macromolecular thin film.

12. The biological detecting method of claim 10, wherein the image sensor is a high-speed CCD camera.

13. The biological detecting method of claim 10, further comprising the steps of:
providing a substrate; and
installing an electric field unit between the substrate and a liquid crystal/polymer composite film.

14. The biological detecting method of claim 13, further comprising the steps of:
providing a power supply to be coupled to the electric field unit to provide an electric field, and using the electric field to change an orientation of the liquid crystal director to change hydrophilic and hydrophobic properties of the liquid crystal/polymer composite film to drive the droplet to move;
connecting a processing unit to the power supply to control the power supply to supply the voltage of the electric field unit; and
connecting the image sensor to the processing unit to capture the droplet on a surface of the liquid crystal/polymer composite film, and generating image data of a hydrophilic/hydrophobic motion caused by a change of the electric field, and providing the image data to the processing unit; wherein the processing unit receives the image data, and analyzes the biological property of the droplet according to the image data.

* * * * *